United States Patent [19]

Carlson et al.

[11] 4,139,303
[45] Feb. 13, 1979

[54] ADAPTIVE COHERENT OPTICAL PROCESSING METHOD AND APPARATUS FOR RECOGNIZING AND COUNTING OBJECTS

[75] Inventors: F. Paul Carlson; Charles K. Lee, both of Seattle, Wash.

[73] Assignee: The Board of Regents of the University of Washington, Seattle, Wash.

[21] Appl. No.: 761,365

[22] Filed: Jan. 21, 1977

[51] Int. Cl.² .................. G01N 33/16; G01N 15/02; G01N 21/00
[52] U.S. Cl. ...................... 356/39; 340/146.3 CA; 356/71; 356/336
[58] Field of Search ............ 356/39, 102–104; 250/222 PC, 550, 574; 340/146.3 F, 146.3 P, 146.3 Q, 146.3 AC, 146.3 CA; 235/92 PC; 350/162 SF

[56] References Cited
U.S. PATENT DOCUMENTS

| 3,469,921 | 9/1969 | Taylor | 356/102 |
| 3,830,569 | 8/1974 | Meric | 356/102 |
| 3,947,123 | 3/1976 | Carlson et al. | 356/39 |

OTHER PUBLICATIONS

Anderson et al., "Counting & Classifying Small Objects by Far-Field Light Scattering", Applied Optics, 7-1971, pp. 1503–1508.

Primary Examiner—John K. Corbin
Assistant Examiner—Wm. H. Punter
Attorney, Agent, or Firm—Christensen, O'Connor, Johnson & Kindness

[57] ABSTRACT

Recognizing and counting geometrically distant objects, such as objects of a particular morphological type (e.g., reticulated red blood cells), located in a field of objects of varying types is disclosed. Coherent light is directed toward a monolayer of objects of various types. The light scattered by the objects is collected by a collecting lens and forms a composite Fourier spectrum at the focal plane of the lens. The Fourier spectrum is selectively analyzed on the basis that each object creates a unique portion of the composite Fourier spectrum, and that a family of objects that are geometrically similar have additive spectrums, when their population is large, randomly located, and nonoverlapping. The analysis is performed by making intensity measurements at radial points in the Fourier plane, weighting the measurements, and summing the result. The radial points and weighting factors are determined using regression techniques.

22 Claims, 5 Drawing Figures

ADAPTIVE COHERENT OPTICAL PROCESSING METHOD AND APPARATUS FOR RECOGNIZING AND COUNTING OBJECTS

BACKGROUND OF THE INVENTION

This invention is directed to object recognition and counting and, more particularly, to recognizing and counting geometrically distinct located objects in a field of objects of varying types.

While this invention was developed for use in detecting and counting particular types of biological cells located in a field of cells of varying types, specifically reticulated red blood cells in a blood sample, and is primarily described in such an environment, it will be appreciated by those skilled in the art and others from the following description that the invention is also useful in other environments. Generally, the invention is useful in any environment where it is desired to recognize and count the number of geometrically similar objects, located in a mass of objects having various geometrical shapes, where the mass of objects can be arrayed in a non-overlapping monolayer. The invention is particularly useful where the objects are small, e.g., cellular in size, but range in equivalent size from 0.01 $\mu$ to 100 $\mu$ for common objects. It should be recognized that larger objects can be imaged to this equivalent size.

For nearly the last two decades biomedical research has focused on automating the acquisition and interpretation of data in cytology and microscopy. A variety of techniques has been proposed and, in some cases, implemented. In many such proposals the optical characteristics of the objects (e.g., cells) have formed the basis of the proposed technique. For example, techniques depending on the optical absorption, fluorescence and scattering properties of cells have been proposed and in some cases used to separate and classify cells. One difficulty with using cellular optical properties to distinguish between cell types is that, since a single cell is examined at a time, chemical reactions are often needed to create or enhance the optical characteristics upon which these techniques depend. As a result, these techniques rely heavily on the ability to create the needed chemical reactions, rather than solely on optical properties. Thus, although continuous flow systems based on optical information can analyze up to several thousand cells per second with a high degree of repeatability, because cell classification depends on external factors (e.g., chemical reactions), the possibility of error is higher and more empirical. Moreover, many of these systems are very dependent on the use of electronic digital computers to perform a variety of time-consuming, and therefore expensive, processing steps. This expense has made such systems particularly undesirable for use in general clinical environments.

As a result of the foregoing difficulties, consideration has been given to the use of optical data processing techniques (as opposed to electronic data processing techniques) to identify and count objects. Optical data processing techniques are based on the knowledge that geometrically distinct objects will scatter light in a distinct manner, and that each geometrically similar object will scatter light in a similar manner.

As will be recognized by those skilled in the data processing art, optical data processing techniques function in an analog, as opposed to a digital, manner. Further, because of the parallel nature of the data processing analog operations can be performed at substantially higher processing rates and with higher data capacity, than can digital operations, particularly in the area of summing data for subsequent analysis.

One of the difficulties in applying optical data processing techniques, as well as other techniques, to the recognition and counting of objects, such as biological cells, is the inherent requirement that the resultant system exactly and unambiguously identify and count the particular cell population desired.

In the past, attempts to meet the foregoing constraint have involved applying matched filter concepts to provide a system wherein only the light scattered by the objects to be recognized and counted is passed. The problem with the use of matched filters is that they suffer from rotational alignment dependencies and, require an unambiguous description of the Weiner spectrum of the cell or object to be recognized and counted.

In many environments the need for an unambiguous or exact count can be met using an estimated count, depending upon the required degree of "exactness." An estimation approach is particularly attractive when the resultant count is to be used for threshold or screening purposes. But, estimation optical data processing systems also have the problem that they require the Weiner spectrum of the desired cell be identified. However, in an estimation system this requirement can be dealt with by using a statistical approach. Specifically, instead of attempting to isolate a single cell for use in identifying or determining the Weiner spectrum of the cells to be counted, an ensemble of cells can be used to form an average spectrum. In this regard, attention is directed to U.S. Pat. No. 3,947,123, issued Mar. 30, 1976 to F. Paul Carlson, et al., for "Coherent Optical Analyzer."

While the optical data processing method and apparatus described in the foregoing patent is an advance over prior methods and apparatus and lends itself to studies of cell types, groups, or subclasses, by simply varying the ensemble selected to develop the average spectrum, it has certain disadvantages. For example, the system is limited by its need to continually fabricate a new Weiner filter for each new class or group to be examined. Further, the method and apparatus implicitly requires that an ensemble of the particular cell to be identified and counted be unambiguously isolated. Obviously, this inflexible filter fabrication requirement significantly limits the extension of this method and apparatus to other environments.

Another previous problem with applying optical data processing tehniques to cell recognition and counting is that of interfacing a coherent optical system to the cells to be counted, both in an input and output sense. In the case of cells on a film slide, the input problem can be readily resolved by creating a monolayer of the cells. However, the output problem remains unless indirect measurements, such as integrating the total output, is acceptable. In many cases, such an indirect measurement is unacceptable or, at best, is less acceptable than desired.

Therefore, it is an object of this invention to provide a new and improved optical data processing method and apparatus for identifying and counting objects.

It is a further object of this invention to provide a new and improved optical data processing method and apparatus for recognizing and counting the number of objects of a particular type in a field of objects of varying types that is based on the geometrical distinctness of the objects.

It is a still further object of this invention to provide an uncomplicated optical data processing method and apparatus suitable for recognizing and counting the number of biological cells of a particular morphological type in a field of biological cells of varying types.

It is also an object of this invention to provide a method of determining the vector positions at which measurements are to be made in a pattern recognition system.

SUMMARY OF THE INVENTION

In accordance with this invention, a method of recognizing and counting geometrically distinct objects located in a field of objects having varying geometrical shapes is provided. The preferred form of the method generally comprises the steps of: directing a beam of coherent light through a monolayer field of objects, including objects of the type to be recognized and counted, such that the objects located in the field scatter the coherent light beam; collecting the scattered light using a Fourier transform lens positioned such that the field is positioned in the focal plane located on one side of the lens; detecting the intensity of the light present at discrete points in the focal (Fourier transform) plane located on the side of the lens opposed to the field side; and, weighting and summing the resultant measurements to obtain an estimate of the number of the objects to be recognized that are located in the field.

In accordance with further principles of this invention, an apparatus for recognizing objects of a particular type located in a monolayer field of objects of varying types is provided. The preferred form of the apparatus of the invention comprises: a source of coherent collimated light forming a beam oriented so as to pass through said field; a collecting lens positioned so as to collect the light scattered by said field, said lens being located a focal length's distance from said field; detecting means for detecting the scattered light collected by said lens at the focal plane of said lens opposite from the focal plane at which said field is located; and, weighting and summing means for weighting and summing the light detected by the detecting means. The detecting means preferably comprises a plurality of light-detecting elements located at equally spaced (discrete) radial positions, i.e., positions that, if located along a common radius extending orthogonally outward from the optical axis defined by said lens, would be equally spaced. This arrangement is particularly useful when the radial positions at which measurements are to be made are initially unknown. Even if known, this arrangement can be utilized merely by using zero weighting factors to eliminate any light measurements made at undesired radial positions. Alternatively, the light-detecting elements may be unequally spaced. This arrangement, i.e., unequal spacing, is particularly useful if the radial measuring positions (which relate to object-identifying frequency points) are known.

It will be appreciated from the foregoing summary that the method and apparatus of the invention does not require the inclusion of a Weiner filter. While an apertured mask may be located at the Fourier transform plane of the lens, such a mask need not have the characteristics of a Weiner filter. Further, while useful in some instances, a mask is not required.

Preferably, the weighting factors applied to the detected light are obtained by regression techniques. The regression techniques are based on the assumption that the objects to be recognized and counted are geometrically distinct from the other objects in the field, whereby each type of object scatters light in a different manner and thus has a different Fourier spectrum. The regression techniques are based on the knowledge that, given enough sampling characteristics of the objects to be recognized and counted, a vector space of the weighting factors can be developed that will adequately describe the particular object space. The regression technique preferred is a least-squares regression technique. In the situation where the radial positions (e.g., frequencies at which measurements to be made) are known, the least-squares regression technique is used to develop weighting factors that allow electronic or digital methods to be utilized to estimate the number of objects to be recognized and counted. In the case where the radial positions are unknown, the regression technique is used to develop both the radial positions and the weighting factors. In the latter situation, if equally spaced detectors are actually included in a physical implementation of the invention, as noted above, selected weighting factors may be made equal to zero, whereby only selected radial positions actually produce the resulting recognition and counting information.

BRIEF DESCRIPTION OF THE DRAWINGS

The foregoing objects and many of the attendant advantages of this invention will become more readily appreciated as the same becomes better understood by reference to the following detailed description when taken in conjunction with the accompanying drawings, wherein.

DESCRIPTION OF THE PREFERRED EMBODIMENT

Prior to describing the invention in detail, a brief discussion of certain background information is presented. As will be readily understood by those skilled in the optical data processing arts, a collimated, coherent light beam passing orthogonally through a monolayer field of objects is scattered by the objects. If this scattered light is collected by a Fourier transform lens, mounted such that the field is located at one focal plane of the lens, a composite Fourier spectrum is formed at the other focal plane of the lens. The composite spectrum includes, in an additive sense, the Fourier spectrum of each object in the field. This result is based in part on the fact that the only change in the spectrum of an object not on the optical axis is a non-measurable phase factor that is lost in the hereinafter described intensity measurement process. The present invention analyzes the composite spectrum and produces an output related to the number of objects of a particular type contributing to the composite spectrum. Thus the invention "recognizes" and "counts" the number of objects of a given type in a field of objects of varying types.

Figure 1:
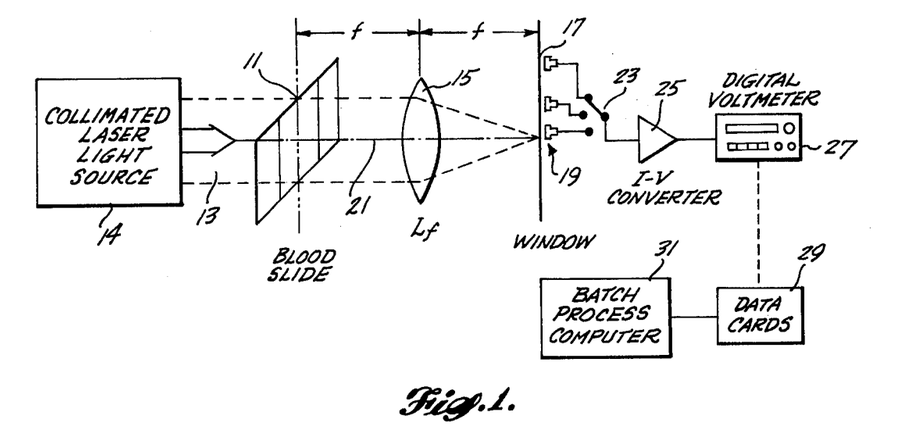
FIG. 1 is a partially block and partially pictorial diagram illustrating an apparatus, formed in accordance with the invention, wherein light is measured at unequally spaced radial positions located in the Fourier transform plane of a lens.
Figure 3:
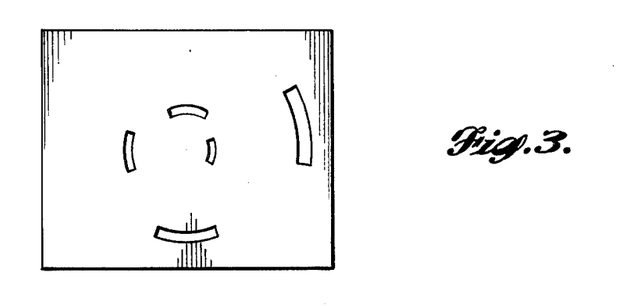
FIG. 3 is a plan view of a window suitable for use in the apparatus illustrated in FIG. 1.

FIG. 1 illustrates an apparatus formed in accordance with the invention for forming and analysing the composite spectrum. The apparatus illustrated in FIG. 1 includes a monolayer of objects, e.g., blood slide 11, mounted orthogonally in a collimated laser light beam 13 created by a collimated laser light source 14. Located on the side of the blood slide 11, remote from the side receiving the collimated light beam 13, is a Fourier transform lens 15. The distance between the blood slide and the Fourier transform lens 15 is equal to the focal length (f) of the transform lens. Located on the opposite side of the Fourier transform lens 15 from the blood slide 11 is a window 17. While in most circumstances the inclusion of a window is not necessary, if included, the window is located at the Fourier plane of the transform lens 15, i.e., in a plane orthogonal to the optical axis 21 defined by the transform lens and spaced from the lens by a distance equal to the focal length (f) of the transform lens 15. A suitable window is illustrated in FIG. 3 and hereinafter described.

Located on the side of the window 17 remote from the transform lens 15, but still at the lens focal plane, are a plurality of photodetectors 19. The photodetectors, as will be better understood from the following description, are located along one or more radii extending orthogonally outward from the optical axis 21 of the transform lens 15, at different radial distances. Alternatively, an approximately mounted mirror may be used to direct the light to detectors located off of the optical axis 21.

In the apparatus illustrated in FIG. 1, the radial distance between adjacent detectors is different; however, it may be the same, as will be better understood from the following discussion. In any event, it is to be understood that the light sensitive surfaces of the detectors lie in the focal plane of the lens, or receive light reflected from the focal plane.

A multiple-pole switch 23 is connected such that each photodetector can be selectively connected to a current-to-voltage converter 25. The output of the current-to-voltage converter is connected to the input of a digital voltmeter 27. The digital voltmeter is adapted to produce individual data cards 29 for each measurement made by a photodetector. The data on the data cards (which could also be recorded on some other memory media) is processed by a batch process computer 31 in combination with known count data, obtained for example by manual counting, to first develop weighting factors. Thereafter the developed weighting factors are used in combination with card data to produce estimated counts, all in the manner hereinafter described.

It is pointed out here that the blood slide is only an example of one type of monolayer object field with which the invention is useful, and that the invention is equally suitable for use with other types of object fields. The only requirement to be met is that different types of objects in the field have different geometrical shapes and that the field be a non-overlapping monolayer field. In the case of a blood slide, the objects include mature red blood cells (erythrocytes), immature red blood cells (reticulocytes), white blood cells (leukocytes), and artifact.

As will be readily appreciated by those skilled in the art, the objects on the blood slide scatter the collimated laser light 13. The light scattered by the objects is collected by the Fourier transform lens 15 and a composite Fourier spectrum is created at the plane of the window 17. The composite Fourier spectrum includes the Fourier spectrum of each of the objects.

Figure 2:
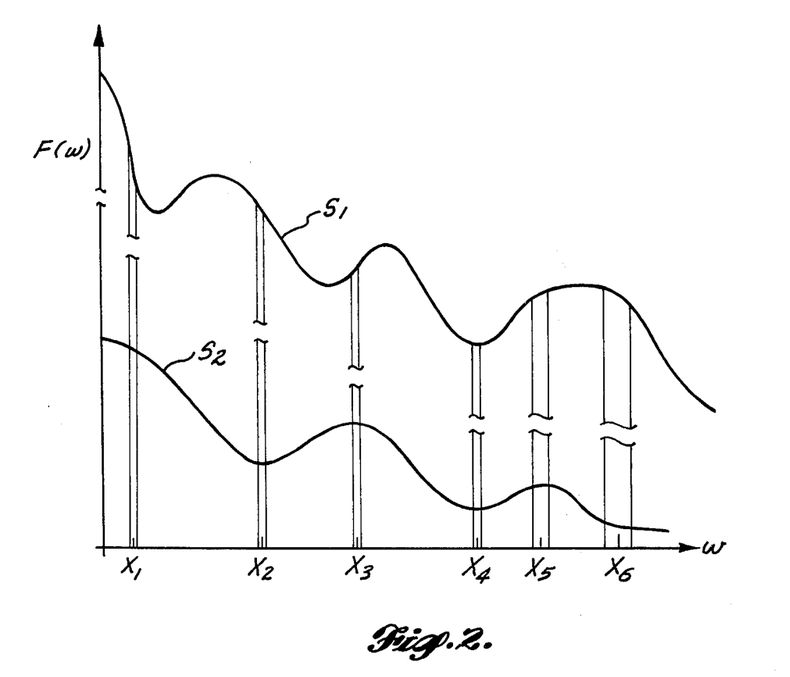
FIG. 2 is a waveform diagram illustrating the light spectrum formed along a radius in the Fourier transform plane of a lens for both a single object and for a field of objects.

FIG. 2 is a waveform diagram illustrating both a typical composite Fourier spectrum $S_1$ and a single object Fourier spectrum $S_2$, taken along one of the radii of the transform plane. The vertical axis denotes beam intensity and the horizontal axis denotes radial or vector positions. As will be readily understood by those familiar with optical Fourier transformation, radial positions are frequency-related.

In accordance with the invention, if light intensity measurements made at suitable radial positions (i.e., $X_1$, $X_2$, etc.) are suitably weighted and, the resultant weighted measurements summed, the result is related to the number of objects of a particular type (e.g., reticulocytes) located in a field of objects of varying types (e.g., a blood slide field). The key, of course, is to appropriately choose the radial positions and correctly weight the measurements made at those positions. In most instances, a particular object creates a wave having hills and valleys (see object spectrum $S_2$ illustrated in FIG. 2). It has been found that if measurements are made at these hills and valleys, i.e., if $X_1$, $X_2$, $X_3$, etc., are located at the hills and valleys of the spectrum of the object to be recognized and counted, and these measurements are appropriately weighted, an accurate estimated count of the number of such objects is provided. In other words, while other radial positions are acceptable in many circumstances, the hills and valleys are acceptable in almost all, if not all circumstances. In some instances, the hill and valley positions are known. For example, prior art devices, such as the one described in U.S. Pat. No. 3,947,123, referenced above, can be used to develop information about the radial position of the hills and valleys of certain cell spectrums, such as a reticulocyte spectrum. When this information is known, obviously the photodetectors are placed at these desired radial positions initially, or if the photodetectors are fixed in position only measurements made by photodetectors located at the desired positions are chosen for use in the weighting and summation steps.

Prior to describing the invention further, a brief discussion of the theory of operation of the invention as best understood is next set forth.

In accordance with the present invention, a model of the vector space defining the objects to be counted is constructed. The model is constructed adaptively through a least-squares procedure by defining a dependent variable $y_i$, which is directly proportional to an observed count of the cells or objects to be counted in terms of a set of independent variables $x_{ij}$, which are proportional to the intensity at certain spatial frequencies (radial positions) of the spectrum, and a set of coefficients $\beta_j$ (weighting factors), which weight the contribution from each $x_{ij}$, such that the resulting sum of the terms is proportional to the desired count. More specifically, $$y_i = \beta_0 + \beta_1 x_{i1} + \ldots + \beta_J x_{iJ} + \epsilon_i, \tag{1}$$

where $i = 1, 2, \ldots, N$, and where $\epsilon_i$ is some random noise or error associated with the observed count, $y_i$. From this model, an unknown $y_i$ can be predicted from measurements of $x_{ij}$, when the appropriate $\beta_j$ are known.

Obviously, development of this model depends upon a determination of the coefficients, $\beta_j$. While the true values of the coefficients or weighting factors cannot be determined without full knowledge of all possible occurrences of $y_i$ and $x_{ij}$, they can be estimated using a least-squares technique based on a set of N observations of $y_i$ and $x_{ij}$. That is, counts made of the number of objects to be recognized and counted located in a random field of objects, made either manually by a technician or by prior art techniques at the same time intensity measurements ($x_{ij}$) are made, can be used to develop $B_j$. More specifically, a term denoting the sum of the squares, S, can be defined by the following equation:

$$S = \sum_{i=1}^{N} [y_i - (\beta_0 + \beta_1 x_{i1} + \ldots + \beta_j x_{ij})]^2 \quad (2)$$

This equation can be rewritten in matrix form as:

$$S = (Y - X\beta)^T (Y - X\beta) \quad (3)$$

where $\beta^T = (\beta_0, \beta_1, \ldots, \beta_j)$, $Y^T = (y_1, y_2, \ldots, y_N)$ and X is a Nx(J+1) matrix. The criterion for selection of the $\beta_j$ elements is to require that S be a minimum, which is equivalent to saying that the sum of the squares of the differences between the observed values and the true values be the least. The least-squares estimates, B, where $B^T = (b_o, b_1, \ldots, b_j)$, are those which minimize the quadratic form of Equation (3) with respect to $\beta$. The procedure to be followed is described in detail in "Applied Regression Analysis" by N. Draper and H. Smith, published by John Wiley & Sons, Inc., New York, 1966, and "The Analysis of Variance" by H. Scheffe, also published by John Wiley & Sons, Inc., 1959, pp. 68-70, and comprises taking the partial derivatives of S with respect to $\beta_j$, setting the resultant matrix equation equal to zero, and, then, replacing $\beta_j$ with the resulting $B_j$. This procedure yields the equation:

$$(X^T X)B = X^T Y, \quad (4)$$

the solution of which can be written as:

$$B = (X^T X)^{-1} X^T Y \quad (5)$$

Thus, the least-squares technique results in the following model for the predicted count $$\hat{y}_i = b_0 + b_1 x_{i1} + b_2 x_{i2} + \ldots + b_j x_{ij} \quad (6)$$

where the estimated cell count is represented by $\hat{y}_i$ and the Weiner spectrum intensity measurements are represented by the $x_{ij}$, taken at specific vector points in the Fourier transform plane (i.e., the focal plane of the lens). For slide N+1 (i.e. the first slide after the weighting factors, $b_j$, have been determined) from the same class of cells, the estimated cell count is given by:

$$\hat{y}_{N+1} = b_0 + b_1 x_{N+1,1} + b_2 x_{N+1,2} + \ldots + b_j x_{N+1,J} \quad (7)$$

which can be written in matrix notation as $$\hat{Y}_{N+1'} = X_{N+1'}^T B \quad (8)$$

where $X_{N+1'}^T = (1, X_{N+1'}, \ldots, X_{N+1,J})$.

Since the count represented by Equations (7) and (8) is just an estimate, there is an inherent error. This error can be described by the variance of the estimation (see the "Applied Regression Analysis" reference cited above) as:

$$V(\hat{Y}_{N+1}) = X_{N+1}^T V(B) X_{N+1} = X_{N'} (X_T X)^{-1} X_{N+1} \sigma^2 \quad (9)$$

where $\sigma^2$ represents the variance of the original count, y. If an estimated variance (see "Statistics: With a View Toward Applications" by L. Brieman, published by Houghton Mifflin, Boston, 1973), $\hat{\sigma}^2$, is now used to describe the variance, $\sigma^2$, where:

$$\hat{\sigma}^2 = (Y - \hat{Y})^T (Y - \hat{Y}) / N - J - 1 \quad (10)$$

then the estimated variance of the N+1 estimated count, $y_{N+1}$, will be given by:

$$\widehat{V(\hat{y}_{N+1})} = X_{N+1}^T (X^T X)^{-1} X_{N+1} \hat{\sigma}^2 \quad (11)$$

Since the prediction model, Equation (6), is constructed from a finite set of training samples, $y_i$, the statistical estimates might be far from being the true values. This is equivalent to saying that the coefficients $b_j$ may vary if the size of the set of "training" samples is changed, or if another set of "training" samples is used. Some way of indicating the accuracy of the estimation is thus necessary. To do this, a 100 $\gamma$% confidence region is used. Inside this region the true prediction model, and hence the true value of the estimates, are all expected to lie in 100 $\gamma$% of the cases. This range of confidence is given by:

$$\hat{y}_{N+1} \pm \sqrt{(J+1) F_{J+1, N-J-1; \gamma} \widehat{V(\hat{y}_{N+1})}} \quad (12)$$

where $F_{J+1, N-J-1; \gamma}$ is the $\gamma$ distribution point of Fisher's F distribution with (J+1) and (N−J−1) degrees of freedom. (See "Statistics: With a View Toward Applications" and "The Analysis of Variance", both referenced above.) This approach provides a more reasonable measurement of the estimation error because it simultaneously adjusts for the variability of all the coefficients $b_j$ that are due to the random observation errors, $\epsilon_i$.

As will be readily appreciated by those skilled in the art, the above analysis is based on the assumptions that: (1) a scheme of selecting and obtaining the independent variables, $x_{ij}$, is known; and, (2) the model formed with these variables is correct. If the model is correct, the estimates, $y_i$, will be unbiased and correct.

To implement this model in a coherent optical processor of the type illustrated in FIG. 1, the problem to be resolved is the selection of the spatial frequency vector components, i.e., the position (or selection) of the detectors whose outputs are to be used, when this information is unknown. Prior to discussing the resolution of this problem a further point is first discussed. Specifically because even particular cells (objects) within a class have a morphological (geometrical shape) variability associated with their size, their spectral amplitudes differ over a range of radial positions. To minimize the variance associated with this amplitude difference, smoothing of the irradiance spectral values is accomplished by using either: (1) a window 19 having finite-sized sampling openings; or, (2) finite-sized detectors, if the window is eliminated. When either of these techniques is used, objects of similar quasicircular morphology, e.g., shape or form, but with variations in azimuthal amplitude, e.g., size, will have a finite dimension in azimuth. In other words, $X_1$, $X_2$, $X_3$, etc., (FIG. 2) will have a finite width determined by size variations. Measurements made over these width variations provide the desired smoothing.

In summary, the sampling system must not only perform discrete sampling in the focal plane, it must also have a smoothing or aperture-averaging effect to compensate for size (but not shape) variations. Either a window of the type illustrated in FIG. 3, or finite sized photodetectors, can be used to achieve this result.

The data obtained by making intensity measurements at each sampling aperture or sampling point from a training set of slides, together with a knowlege of the values of the dependent variables (counts of the desired objects), $y_i$, are used to find the weighting coefficients, B, in accordance with Equation (5). This knowledge is then used in accordance with Equation (8) to subsequently predict or estimate the number of objects, $Y_{N+1}$.

Turning now to the spatial frequency vector component problem denoted above, in the foregoing discussion, the $x_{ij}$ sampling points (vector components) were assumed to be known, based on knowledge of the object or cell to be counted. More precisely, the scattering pattern based on the geometrical distinctures or morphology of the object or cell to be counted was assumed to be known. And, the selection of the $x_{ij}$ sampling points was made in an ad hoc fashion, based on this prior knowledge of the Weiner spectrum (scattering pattern) of the particular objects to be recognized and counted. In some situations, such knowledge may not be readily available. Thus, in order to make the system totally adaptive to recognizing and counting objects of one particular morphological type in a field of objects of varying morphological types, a technique for determining not only the weighting coefficients, B, but also the $x_{ij}$ positions, is necessary. In accordance with the invention, a mechanism for selecting the optimum $X_{ij}$ vector components is provided. Prior to describing the preferred way of selecting the $x_{ij}$ vector components, it is pointed out that an uncomplicated way of obtaining this information is to transform a uniform set of $x_{ij}$ vector components to new normalized components, $x'_{ij}$, and then correlate the independent and dependent variables ($x'_{ij}$ and $y_i$). From the resulting correlation matrix, those independent variables, $x'_{ij}$, which are highly correlated with the dependent variables, $y_i$, can be used to form the desired model, i.e., to describe the vector space by defining the position at which the $x'_{ij}$ measurements are to be made. This method, however, is unsatisfactory in that it works in general only when the independent variables are orthogonal or weakly correlated with each other. Thus, a different procedure, hereinafter described, for orthogonalizing the resulting vector space is preferred. More specifically, in accordance with the invention, the preferred way of selecting the independent variables, $x'_{ij}$, (that is, the position at which measurements are to be made) is to build up the vector space model in a stepwise regression process. In this regard, attention is directed to "Applied Regression Analysis," referenced above.

A stepwise regression process makes use of the partial F-value test of the variables at each step before and after a variable is included in the model. In terms of the present invention, the partial F-value may be defined as:

$$F_p = \frac{ss(b_j|b_o,b_1,...,b_{j-1},b_{j+1},...,b_k)}{ss(b_o,...,b_j,...,b_k)/(N-k-1)} \quad (13)$$

where
$j = 1, 2, \ldots, K$;
$ss(b_o, \ldots, b_k) = [Y - \hat{Y}(b_o, \ldots, b_k)]^T[Y - \hat{Y}(b_o, \ldots, b_k)]$ which equals the sum of squares of residuals when the model has $k+1$ independent variables including the constant term; and $ss(b_j|b_o, \ldots, b_{j-1}b_{j+1}, \ldots, b_k)$ equals the extra sum of the squares of the residuals when the $j^{th}$ variable is not included, which is also equals a measure of the value of adding a $\beta_j$ term to a model that originally did not include such a term. If equation (13) results in $F_p > F_{1,N-k-1;\gamma}$, the $j^{th}$ variable, i.e., the variable being analyzed, will be included or retained. If this test is not passed, the $j^{th}$ variable is dropped. The test procedure is sequentially applied to all variables, i.e., an Equation (13) calculation is made for all variables and the resulting $F_p$ values are tested to see if they are greater than $F_{1,N-k-1;\gamma}$.

Even though the inclusion of the $j^{th}$ variable may produce a substantial reduction of the total sum of squares, its presence in the model will not be significant if it has a large probability of having a null value. Thus, an F-value test defined as $$F_b = b_j^2 / V(b_j) \quad (14)$$

where $V(b_j)$ is the variance of the coefficient $b_j$ and is used to determine the significance of each chosen coefficient (weighing factor). The coefficient, and thus its related $x'_{ij}$ position, is significant if $F_b > F_{1,N-k-1;\gamma}$, or equivalently $x'_{ij}$, should be present in $100_\gamma\%$ of the cases.

After the model has been constructed with the $x'_{ij}$ ($j = 1,2,\ldots,J$) variables, the goodness of the fit is checked using an $R^2$ ratio test and an F-value test defined, respectively, as $$R^2 = (\hat{Y} - \bar{Y})^T(\hat{Y} - \bar{Y})/(Y - \bar{Y})^T(Y - \bar{Y}) = \quad (15)$$
$$1 - (\hat{Y} - Y)^T(\hat{Y} - Y)/(Y - \bar{Y})^T(Y - \bar{Y})$$

and
$$F = [(\hat{Y} - \bar{Y})^T(\hat{Y} - \bar{Y})/(\hat{Y} - Y)^T(\hat{Y} - Y)](N - J - 1/J) \quad (16)$$

where
$$(\hat{Y} - \bar{Y})^T = (\hat{y}_1 - \bar{y}, \hat{y}_2 - \bar{y}, \ldots, \hat{y}_N - \bar{y}) \quad (17)$$

and
$$\bar{y} = \frac{1}{N} \sum_{i=1}^{N} y_i \quad (18)$$

The $R^2$ ratio test gives the fraction of the total variation of the observations that are accounted for by the fitted model. A value of unity for $R^2$ indicates that all the estimates $y_i$ coincide exactly with the observations, $\hat{y}_i$. The F-value test indicates that the model as a whole produces significant reduction of residual errors when $F > F_{J,N-J-1;\gamma}$.

Whether the estimates $y_i$ are biased or not depends on the independent variables $x_{ij}$ used in the model. The estimates may be statistically checked (see "Fitting Equations to Data" by C. Daniel and F. S. Wood, published by John Wiley & Sons, Inc., New Yor, 1971, pp. 86-87) by the following equation:

$$C_p = (Y - Y_p)^T(Y - Y_p)/\sigma^2 - (N - 2P) \quad (19)$$

where $\hat{Y}_p$ are the estimates from a model with p independent variables; and $x_{ij}$, j = 1,2, ... ,p−1, including the constant term, and $\hat{\sigma}^2$ is the best estimate of $\sigma^2$, determined by some other means (see "Applied Regression Analysis", referenced above). $C_p$ is the estimate of the standardized total squared error (bias plus the random component ) of the prediction model. When the p-term model has negligible bias, $C_p \simeq$ p.

Figure 4:
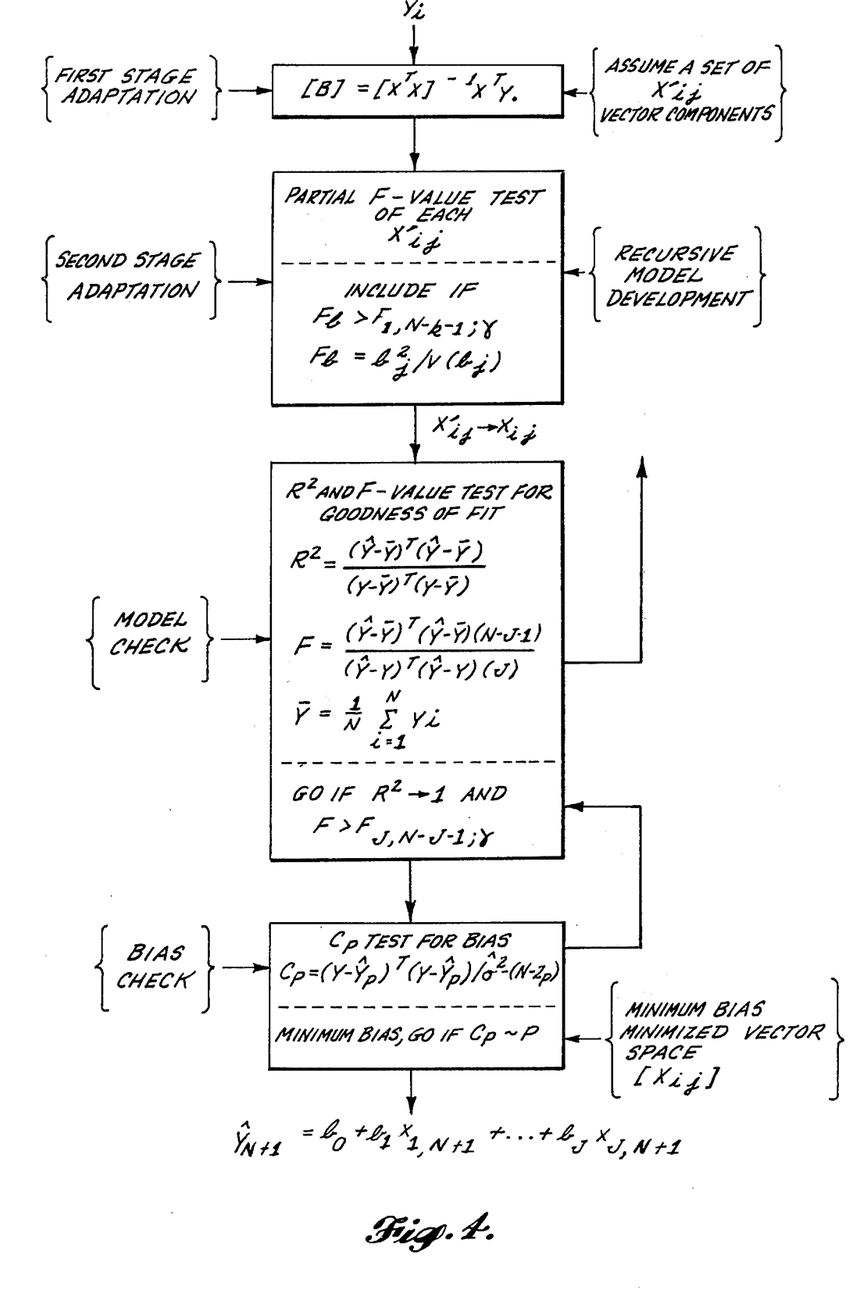
FIG. 4 is a flow diagram illustrating a sequence of steps used to determine weighting factors and radial positions, all in accordance with the invention; and, FIG. 5 is a partially block and partially pictorial diagram illustrating an apparatus, formed in accordance with the invention, wherein light measurements are made at equally spaced radial positions located in the transform plane of a lens.

FIG. 4 is a block diagram illustrating in detail the use of the foregoing sequence to develop a model or equation useful in estimating (e.g., recognizing and counting) objects. In this sequence, the vector space samples are built up term by term through the use of partial F-value tests. More specifically, a set of $x'_{ij}$ vector components are first assumed for a known $Y_i$ count (made manually or via prior art techniques). This assomption may be made by mounting the detectors in predetermined radial positions, or by sensing the outputs of only selected detectors of a series of detectors located at fixed radial positions. In any event partial F-value tests are made of each $x'_{ij}$ component (based on the known $y_i$ counts), and they are included if the $F_b$ tests described above are met. If the $F_b$ tests are not met, the $x'_{ij}$ components are rejected because they have a high probability of having a null or negligable value. Once a trial model (equation) is developed, the goodness of fit is checked by the $R^2$ and F-value tests as discussed above. If the fit is inadequate, the sequence is repeated, i.e., another set of $x'_{ij}$ components are assumed, and the step are repeated. Once a model with a reasonable fit is developed, bias is checked and, if below a minimum level, the resultant model or equation is chosen for use in producing an estimated count of similar objects in a field of objects having an unknown actual count, i.e., $y_i$ is unknown.

At this point it will be appreciated that two different techniques for developing an estimation model or equation have been discussed. The first technique is based or prior knowledge of the $x_{ij}$ vector position. When this information is available, the weighting components, B, are developed using a least-squares procedure. If the $x_{ij}$ vector component information is unknown, $x_{ij}$ information, as well as weighting factor information, are simultaneously developed utilizing the stepwise regression process discussed above, in combination with the F-value, $R^2$ and bias tests also discussed above, all of which are illustrated in FIG. 4. In either case, both the weighting factors, B, and the $X_{ij}$ vector positions are either known or produced. After the necessary B and $x_{ij}$ information is developed, slide light intensity measurements made at the chosen vector positions in the Fourier plane are weighed by the related weighting factors, and the weighted values are summed, all in accordance with Equation (8), to provide an estimated object count. In this manner, an estimate of the number of objects of a particular morphological type in a field of objects of various morphological types, is produced.

Figure 5:
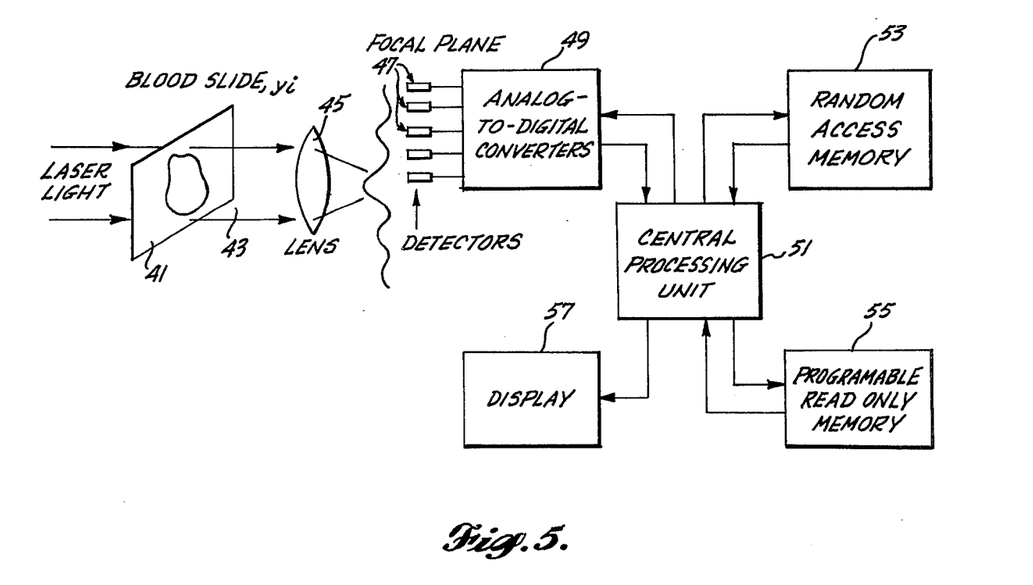

FIG. 5 is a partially block and partially schematic diagram illustrating in more detail a preferred embodiment of a system formed in accordance wih the invention for producing an estimated count of a number of objects of a particular type (e.g., reticulocytes) contained in a monolayer field of objects of varying types (e.g., reticulocytes, erythrocytes, blood artifact, etc.). the apparatus illustrated in FIG. 5 includes a blood slide 41 orthogonally arrayed in a laser light beam 43. A Fourier transform lens 45 is located on the side of the blood slide remote from the side receiving the laser light beam 43. The focal lens 45 is located a focal length's distance from the blood slide.

A plurality of detectors 47 are located at the focal plane of the Fourier transform lens 45 on the side opposite the blood slide. As discussed above, it is at this plane that the composite Fourier spectrum is formed. The detectors may be equally spaced from one another along a radius projecting orthogonally outwardly from the optical axis defined by the lens 45; or, they may be located on different radii which, if made common, would result in the detectors being equally spaced. Preferably the spacing between detectors is very small whereby substantially the entire region covered by a radial line is covered either along a single radius or along several radii.

The detectors are each connected to an analog-to-ditigal converter 49; or, the detectors are each selectively connected to a single analog-to-digital converter. The analog-to-digital converter outputs are applied to a central processing unit 51. The central processing unit 51 is adapted to control the analog-to-digital converts 49 such that a converted signal from each photodetector is applied to the central processing unit 51 if and when required. Also illustrated and connected to the central processing unit 51 are: a random access memory (RAM) 53; a programmable read-only memory (PROM) 55; and, a display 57.

In operation, a series of "training" slides, wherein the object (e.g., reticulocyte) count, $y_i$, is known, are sequentially first placed in the laser light beam in the position depicted by the blood slide 41. For each blood slide, each of the detectors has its output sensed, converted, and stored in a suitable storage position in the RAM 53. After the series of "training" slides has been processed, the data stored in the RAM is processed by the central processing unit 51 in accordance wih a program stored in the PROM 55. The stored program causes the central processing unit to function in accordance with the flow diagram illustrated in FIG. 4 and previously discussed. As a result of this processing, both $X_{ij}$ vector position and B weighting factor information are developed. Thereafter, when a slide having an unknown count is placed in the laser light beam 43, the central procesing unit controls the analog-to-digital converters, such that only the detectors located at the developed $x_{ij}$ positions are "read." The resulting data is then weighted by the developed weighting factors, B, and the result summed to create an estimated count value, which is applied to the display 57.

In one actual embodiment of the present invention, significant error reduction over previous systems, such as the system disclosed in U.S. Pat. No. 3,947,123, was found. The error was found to be only limited by the number of training slides utilized. For a reasonable number of training slides, e.g., 25, the estimated count error was found to be less than 2%. Further, in this actual embodiment of the invention, laser illumination was obtained from an argon-ion laser operating in a single-mode configuration. The scattered light present in the transform plane was collected by pin photodetectors after reflection from a hexagonal mirror system mounted at the focal plane. The mirror system was necessitated by the physical size of the pin detectors. A more preferred detecting arrangement results if charged injection device (CID) or charge coupled device (CCD) detection arrangements are used.

While a preferred embodiment of the invention has been illustrated and described, it will be appreciated by those skilled in the art and others that various changes can be made both to the method and apparatus of the invention without departing from its spirit and scope. All the invention requires is that the objects to be detected and counted have some geometrical (e.g., morphological) distinctness wih respect to the other objects located in the field of objects being analyzed; and, that the objects be susceptible to being arrayed in a non-overlapping monolayer field. It will also be appreciated that the invention also includes a novel method of determining the vector positions at which measurements are to be made in a pattern recognition system, which is useful in environments other than those in which both recognition and counting is desired. For example, the method is useful in environments where recognition alone is desired. Finally, while a particular type of processing apparatus has been illustrated and described, it will be appreciated that the other types of processing apparatus can also be utilized. Hence, the invention can be practiced otherwise than as specifically described herein.

The embodiments of the invention in which an exclusive property or privilege is claimed are defined as follows:

1. A method of recognizing and counting randomly sized, randomly located and randomly oriented objects of a distinct geometrical shape in a mass of objects of varying geometrical shapes, said method comprising the steps of:
   arraying said mass of objects in a non-overlapping field;
   passing a beam of coherent light through said non-overlapping field such that said field scatters said beam of coherent light;
   positioning a Fourier transform lens such that the lens collects light scattered by said non-overlapping field and forms a composite Fourier spectrum of said non-overlapping field;
   measuring the intensity of the light at selected points in said composite Fourier spectrum; and,
   combining said light intensity measurements by nonuniformly weighting each light intensity measurement made by a predetermined weighting factor, B; and, summing said nonuniformly weighted light intensity measurements to provide an estimated count of the number of objects of a distinct geometrical shape located in said non-overlapping field.

2. A method of recognizing and counting randomly sized, randomly located and randomly oriented objects of a distinct geometrical shape in a mass of objects of varying geometrical shapes as claimed in claim 1 wherein:
   said non-overlapping field is positioned orthogonal to said beam of coherent light; and,
   said Fourier transform lens is positioned a focal length's distance from said non-overlapping field on the side thereof remote from the side receiving said beam of coherent light, whereby said Fourier spectrum is formed a focal length's distance from said Fourier transform lens.

3. A method of recognizing and counting randomly sized, randomly located and randomly oriented objects of a distinct geometrical shape in a mass of objects of varying geometrical shapes as claimed in claim 2 wherein:
   said objects of a distinct geometrical shape produce a Fourier spectrum having hills and valleys; and,
   at least some of the selected positions at which said light intensity measurements are made are located at some of the hills and valleys of the Fourier spectrum produced by said objects of a distinct geometrical shape.

4. A method of recognizing and counting randomly sized, randomly located and randomly oriented objects of a distinct geometrical shape in a mass of objects of varying geometrical shapes as claimed in claim 3 wherein said weighting factors, B, are determined by using regression techniques based on measurements made using training non-overlapping fields wherein the number of objects of said distinct geometrical shape is known.

5. A method of recognizing and counting randomly sized, randomly located and randomly oriented objects of a distinct geometrical shape in a mass of objects of varying geometrical shapes as claimed in claim 2 wherein said selected points at which said light intensity measurements are made and said weighting factos, B, are determined by using regression techniques based on measuremens made using training non-overlapping fields wherein the number of objects of said distinct geometrical shape is known.

6. A mehod of recognizing and counting randomly sized, randomly located and randomly oriented objects of varying geometrical shapes as claimed in claim 2 wherein said weighting factors, B, are determined by using regression techniques based on measurements made using training non-overlapping fields wherein the number of objects of said distinct geometrical shape is known.

7. A method of recognizing and counting randomly sized, randomly located and randomly oriented objects of a distinct geometrical shape in a mass of objects of varying geometrical shapes as claimed in claim 1 wherein said selected points at which said light intensity measurements are made and said weighting factors, B, are determined by using regression techniques based on measurements made using training non-overlapping fields wherein the number of objects of said distinct geometrical shape is known.

8. A method of recognizing and counting randomly sized, randomly located and randomly oriented cells of a distinct morphology, such as reticulocytes, in a mass of cells of varying morphology, such as a blood sample, said method comprising the steps of:
   arraying said mass of cells on a slide so as to form a non-overlapping field;
   passing a beam of coherent light through said non-overlapping field of cells such that said field scatters said beam of coherent light;
   positioning a Fourier transform lens such that the lens collects light scattered by said non-overlapping field of cells and forms a composite Fourier spectrum of said non-overlapping field;
   measuring the intensity of the light at selected points in said composite Fourier spectrum; and,
   combining said light intensity measurements by nonuniformly weighting each light intensity measurement mode by a predetermined factor, B; and summing said nonuniforly weighted light intensity measurements to provide an estimated count of the number of cells of said distinct morphology located in said non-overlapping field of cells.

9. A method of recognizing and counting randomly sized, randomly located and randomly oriented cells of a distinct morphology in a mass of cells of varying morphology as claimed in claim 8 wherein:
said slide containing said non-overlapping field of cells is positioned orthogonal to said beam of coherent light; and,
said Fourier transform lens is positioned a focal length's distance from said non-overlapping field of cells on the side thereof remote from the side receiving said beam of coherent light, whereby said Fourier spectrum is formed a focal length's distance from said Fourier transform lens.

10. A method of recognizing and counting randomly sized, randomly located and randomly oriented cells of a distinct morphology in a mass of cells of varying morphology as claimed in claim 9 wherein:
said cells of a distinct morphology produce a Fourier spectrum having hills and valleys; and,
at least some of the selected points at which said light intensity measurements are made are located at some of the hills and valleys of the Fourier spectrum produced by said cells of a distinct morphology.

11. A method of recognizing and counting randomly sized, randomly located and randomly oriented cells of a distinct morphology in a mass of cells of varying morphology as claimed in claim 10 wherein said weighting factors, B, are determined by using regression techniques based on measurements made using training slides wherein the number of cells of said distinct morphology is known.

12. A method of recognizing and counting randomly sized, randomly located and randomly oriented cells of a distinct morphology in a mass of cells of varying morphology as claimed in claim 9 wherein said selected points at which said light intensity measurements are made and said weighting factors, B, are determined by using regression techniques based on measurements made using training slides wherein the number of cells of said distinct morphology is known.

13. A method of recognizing and counting randomly sized, randomly located and randomly oriented cells of a distinct morphology in a mass of cells of varying morphology as claimed in claim 8 wherein said weighting factors, B, are determined by using regression techniques based on measurements made using training slides wherein the number of cells of said distinct morphology is known.

14. A method of recognizing and counting randomly sized, randomly located and randomly oriented cells of a distinct morphology in a mass of cells of varying morphology as claimed in claim 8 wherein said selected points at which said light intensity measurements are made and weighting factors, B, are determined by using regression techniques based on measurements made using training slides wherein the number of cells of said distinct morphology is known.

15. Apparatus for recognizing and counting randomly sized, randomly located and randomly oriented objects of distinct geometrical shape in a mass of objects of varying geometrical shapes, said appratus comprising:
light means for producing a collimated coherent light beam;
support means for supporting, in a non-overlapping field, a mass of objects of varying geometrical shapes in said coherent light beam;
transform lens means, mounted on the side of said support means remote from the side receiving said coherent light beam, for collecting light scattered by the mass of objects supported by said support means in a non-overlapping field and forming said collecting light into a composite Fourier spectrum of the mass of objects forming said non-overlapping field;
light detecting means mounted so as to detect the intensity of the light at selected points in the Fourier spectrum produced by said transform lens means and produce output signals having a parameter related to the intensity of the light detected at said selected points in said Fourier spectrum; and,
combining means connected to said light detecting means for receiving said output signals having a parameter related to the intensity of the light detected by said light detecting means, nonuniformly weighting selected ones of said received output signals and summing the resultant nonuniformly weighted signals to produce a combined output signal having a parameter related to the number of objects of a distinct geometrical shape located in said non-overlapping field.

16. Apparatus for recognizing and counting randomly sized, randomly located and randomly oriented objects of a distinct geometrical shape in a mass of objects of varying geometrical shapes as claimed in claim 15 wherein said transform lens means is located a focal length's distance from said support means and wherein said composite Fourier spectrum is formed at the focal plane of said transform lens means located on the side of said lens means remote from the side on which said support means is located.

17. Apparatus for recognizing and counting randomly sized, randomly located and randomly oriented objects of a distnct geometrical shape in a mass of objects of varying geometrical shapes as claimed in claim 16 wherein:
said transform lens means defines an optical axis;
said support means and said light detecting means lie in planes orthogonal to said optical axis; and,
said selected points at which said light detecting means detect light in the Fourier spectrum produced by said transform lens means are located at predetermined radial positions in the plane in which said light detecting means lies.

18. Apparatus for recognizing and counting randomly sized, randomly located and randomly oriented objects of a distinct geometrical shape in a mass of objects of varying geometrical shapes as claimed in claim 17 wherein:
said light detecting means produce analog signals whose magnitude is related to the intensity of the light detected by said light detecting means;
said combining means includes analog-to-digital converting means connected to said light detcting means for converting said analog signals into digital signals; and,
said combining means also includes calculating means connected to said analog-to-digital converting means for nonuniformly weighting said digital signals and summing the resulting nonuniformly weighted digital signals.

19. A method of determining the vector positions, $X_{ij}$, at which light intensity measuremments are to be made in a pattern recognition system for recognizing geometrically distinct objects that includes a source of coherent energy positioned so as to direct a beam of coherent energy through a mass of objects located in a monolayer field and a fourier transform lens positioned so as to collect energy scattered by the objects forming said monolayer field and form a composite fourier spectrum thereof, said method comprising the steps of:

assuming a set of vector positions $x'_{ij}$;

making energy intensity measurements at each assumed vector position $x'_{ij}$, for each one of a training set of monolayer fields having a known parameter related to the objects to be recognized;

performing a partial F-value test using the results of said measurements for each assumed vector position, $x'_{ij}$; and, testing the results of each partial F-value test to determine if the result is greater than $F_{1,N-k-1;\gamma}$ where $\gamma$ is the gamma distribution point of Fisher's F distribution of 1 and $N-k-1$ degrees of freedom, N is equal to the number of samples used in the training set and k is the total number of vector positions $x_{ij}$ to be determined; and, choosing the assumed vector positions, $x'_{ij}$, to be vector positions, $x_{ij}$, at which measuremens are to be made if the result of their related partial F-value test is greater than $F_{1,N-k-1;\gamma}$.

20. A method of choosing the vector positions, $x_{ij}$, at which measurements are to be made in a pattern recognition system as claimed in claim 19 including the further step of determining if each assumed variable, $x'_{ij}$, that has a partial F-value test result greater than $F_{1,N-k-1;\gamma}$, has a large probability of having a null value and rejecting the assumed variables, $x'_{ij}$, that have a large probability of having a null value prior to choosing which assumed vector positions $x'_{ij}$ are to be vector positions $x_{ij}$.

21. A method of choosing the vector positions, $x_{ij}$, at which measurements are to be made in a pattern recognition system comprising the steps of:

assuming a set of vector positions, $x'_{ij}$;

making energy intensity measurements at each assumed vector position, $x'_{ij}$, for each one of a training set of items;

performing a partial F-value test using the results of said measurements for each assumed vector positions, $x'_{ij}$; and, testing the results of each partial F-value test to determine if the result is geater than $F_{1,N-k-1;\gamma}$ where $\gamma$ is the gamma distribution point of Fisher's F distribution with 1 and $N-k-1$ degrees of freedom, N is equal to the number of samples used in the training set and k is the total number of vector positions $x_{ij}$ to be determined; and, choosing the assumed vector positions, $x'_{ij}$, to be vector positions, $x_{ij}$, at which measurements are to be made if the result of their related partial F-value test is greater than $F_{1,N-k-1;\gamma}$.

22. A method of choosing the vector positions, $x_{ij}$, at which measurements are to be made in a pattern recognition system as claimed in claim 21 including the further step of determining if each assumed variable, $x'_{ij}$, that has a partial F-value test result greater than $F_{1,N-k-1;\gamma}$, has a large probability of having a null value and rejecting the assumed variables, $x'_{ij}$, that have a large probability of having a null value prior to choosing which assumed vector positions $x'_{ij}$ are to be vector positions $x_{ij}$.

* * * * *

UNITED STATES PATENT AND TRADEMARK OFFICE
CERTIFICATE OF CORRECTION

PATENT NO. : 4,139,303
DATED : February 13, 1979
INVENTOR(S) : Carlson et al.

It is certified that error appears in the above-identified patent and that said Letters Patent are hereby corrected as shown below:

Col. 3, line 6, delete "it" and insert —It—.

Col. 8, line 15 (Eq. 10), delete ",$\sigma^2 = (Y-Y)^T(Y-Y)/N-J-1$" and insert —$\sigma^2 = (Y-\hat{Y})^T(Y-\hat{Y})/N-J-1$—.

Col. 10, line 11, delete "K" and insert —k—.
Col. 11, line 1, delete "Yor" and insert —York—.

Col. 11, line 3 (Eq. 19), delete "$Cp = (Y-Yp)^T(Y-Yp)/\sigma^2 - (N-2P)$" and insert —$Cp = (Y-\hat{Yp})^T(Y-\hat{Yp})/\sigma^2 - (N-2P)$—.

Col. 11, line 11, delete "component )" and insert —component)—.
Col. 11, line 20, delete "assomption" and insert —assumption—.
Col. 11, line 62, delete "wih" and insert —with—.
Col. 12, line 47, delete "procesing" and insert —processing—.
Claim 5, line 24 (Col. 14), delete "factos" and insert —factors—.
Claim 5, line 26 (Col. 14), delete "measuremens" and insert —measurements—.
Claim 6, line 30 (Col. 14) delete "mehod" and insert —method—.
Claim 8, line 67 (Col. 14), delete "uniforly" and insert —uniformly—.
Claim 15, line 65 (Col. 15), delete "appratus" and insert —apparatus—.
Claim 17, line 41 (Col. 16), delete "distnct" and insert —distinct—.
Claim 18, line 61 (Col. 16), delete "detcting" and insert —detecting—.

UNITED STATES PATENT AND TRADEMARK OFFICE
CERTIFICATE OF CORRECTION

PATENT NO. : 4,139,303
DATED : February 13, 1979
INVENTOR(S) : Carlson et al.

It is certified that error appears in the above-identified patent and that said Letters Patent are hereby corrected as shown below:

Claim 19, line 2 (Col. 17), delete "measuremments" and insert --measurements--.

Claim 21, line 15 (col. 18), delete "greater" and insert --greater--.

Signed and Sealed this

Twenty-fifth Day of September 1979

[SEAL]

Attest:

LUTRELLE F. PARKER

*Attesting Officer*    *Acting Commissioner of Patents and Trademarks*